United States Patent [19]

Ellis et al.

[11] Patent Number: 5,310,668
[45] Date of Patent: May 10, 1994

[54] VARICELLA-ZOSTER VIRUS AS A LIVE RECOMBINANT VACCINE

[75] Inventors: Ronald W. Ellis, Overbrook Hills, Pa.; Elliott Kieff, Brookline, Mass.; Edward M. Scolnick, Wynnewood; Robert S. Lowe, Harleysville, both of Pa.

[73] Assignee: Merck & Co., Inc., Rahway, N.J.

[21] Appl. No.: 846,751

[22] Filed: Feb. 27, 1992

Related U.S. Application Data

[63] Continuation of Ser. No. 376,788, Jul. 7, 1989, abandoned, which is a continuation-in-part of Ser. No. 276,984, Nov. 28, 1988, abandoned, which is a continuation of Ser. No. 263,562, Oct. 27, 1988, abandoned, which is a continuation of Ser. No. 51,444, May 18, 1987, abandoned, which is a continuation-in-part of Ser. No. 20,617, Mar. 2, 1987, abandoned, which is a continuation-in-part of Ser. No. 876,956, Jun. 20, 1986, abandoned.

[51] Int. Cl.$^5$ .............. C12N 15/86; C12N 7/01; A61K 39/295; A61K 39/25
[52] U.S. Cl. .............. 435/172.3; 435/235.1; 435/300.1; 424/89; 935/32; 935/57; 935/65
[58] Field of Search .............. 435/235.1, 320.1, 172.3, 435/69.1, 69.3; 424/89; 935/32, 57, 65

[56] References Cited

U.S. PATENT DOCUMENTS

| | | | |
|---|---|---|---|
| 4,769,331 | 9/1988 | Roizman et al. | 435/172.3 |
| 4,999,296 | 3/1991 | Kit et al. | 435/235.1 |

FOREIGN PATENT DOCUMENTS

| | | | |
|---|---|---|---|
| 0074808 | 3/1983 | European Pat. Off. | C12N 15/00 |
| WO8302393 | 7/1983 | PCT Int'l Appl. | A61K 39/12 |
| 8600528 | 1/1986 | PCT Int'l Appl. | A61K 39/02 |
| 9002191 | 3/1990 | PCT Int'l Appl. | C12N 15/86 |

OTHER PUBLICATIONS

Post, L. E. et al. 1981, *Cell* vol. 25 p. 227–232.
Roizman, B. et al. 1985. *Science* vol. 229 p. 1208–1214.
Gelb, L. D. 1985. In *Virology*, ed. B. N. Fields et al, Raven Press, NY, p. 604.
Valenzuela et al. *Biotechnology* 3, pp. 323–326 (1985).
Sawyer et al. *Virology* 149, pp. 1–9 (1986).
Buller et al. *Nature* 317, pp. 813–815 (1985).
Shiraki et al. *Biological Abstracts* 77, ab 56235 (1983).
Gershon et al. *Biological Abstracts* 78, ab. 75715 (1984).
Perkus et al. *Science* 229 pp. 981–984 (1985).
Poffenberger et al. *Proc. Nat. Acad. Sci.* USA 80, pp. 2690–2694 (1983).
Desrosiers et al. *Molecular & Cellular Biol.*, 5, pp. 2796–2803 (1985).
Keeler et al. *Gene* 50, pp. 215–224 (1986).
Lowe et al. *Proc. Nat. Acad. Sci.* USA 84, pp. 3896–3900 (1987).
Emini et al. *Biological Abstracts* 82 ab. 14622 (1986).
Wedderburn et al. *Biological Abstracts* 79, ab. 59632 (1984).
Provost et al. *Biological Abstracts* 84 ab. 120239 (1987).
Gilden, et al., *J. Gen. Virol.* 60, 371–374 (1982).
Shiraki et al. *Biken Journal* 26, pp. 17–23 (1983).
Gershon et al. *JAMA* 252 pp. 355–362 (1984).
Grose et al. *Biken Journal*, 26 pp. 1–15, (1983).
Yamanishi, K. et al. *Infection and Immunity* 28(2) pp. 536–541, (1980).

(List continued on next page.)

*Primary Examiner*—Richard A. Schwartz
*Assistant Examiner*—Mary E. Mosher
*Attorney, Agent, or Firm*—Gerard H. Bencen; Jack L. Tribble; Paul D. Matukaitis

[57] ABSTRACT

A vaccine strain of varicella-zoster virus (VZV), tested in clinical trials, is capable of preventing chickenpox in children. This virus has been modified by the introduction into its genome of heterologous DNA which encodes an immunogenic polypeptide of another human pathogen. This heterologous polypeptide is expressed in cells infected by the recombinant virus. Such recombinant VZV is useful as a vaccine for chickenpox as well as for heterologous pathogens.

13 Claims, 5 Drawing Sheets

OTHER PUBLICATIONS

Ostrove, J. M. et al. *J. Virology,* 56, (2) pp. 600-606 (1985).

Edson et al. *Virology,* 145, pp. 62-71, (1985).

Maguire, H. F., and Hyman, R. W. *Intervirology,* 26, pp. 181-191, (1986).

Wolff, M. H., *Med. Microbiol. Immunol.,* 166, 21-28, (1978).

Shiraki, K.., and Takahashi, M. *J. Gen. Virol.,* 61, 271-275, (1982).

Roizman, B., and Spear, P. G., *J. of Virology,* 2, (1) pp. 83-84, (1967).

Garfinkle, B., McAuslan, B. R. *Proc. Natl. Acad. Sci., USA,* 71, pp. 220-224 (1974).

Lee, G., et al., *Proc. Natl. Acad. Sci.* USA, 79, pp. 6612-6616, (1982).

Lowe, R., et al., *Vaccines* 88, Cold Spring Harbor, pp. 185-188 (1988).

Peden, K. et al., *Cell, 31,* 71-80 (1982).

ILTIS, J. et al., *Virology,* 82, pp. 345-352 (1977).

Ellis, R. W. et al., Tech. Advs. in Vaccine Dev. pp. 235-241 (1988).

Davison, A. J. et al., *J. Gen. Virol.* 67 597-611 (1986).

Ecker & Hyman *Proc. Natl. Acad. Sci.* USA 79, pp. 156-160 Jan. (1982).

Shiraki, K. et al., *J. Gen. Virol.* 72, pp. 1393-1399 (1991).

Miller et al. *J. Exp. Med.* 147, 948-967 (1977).

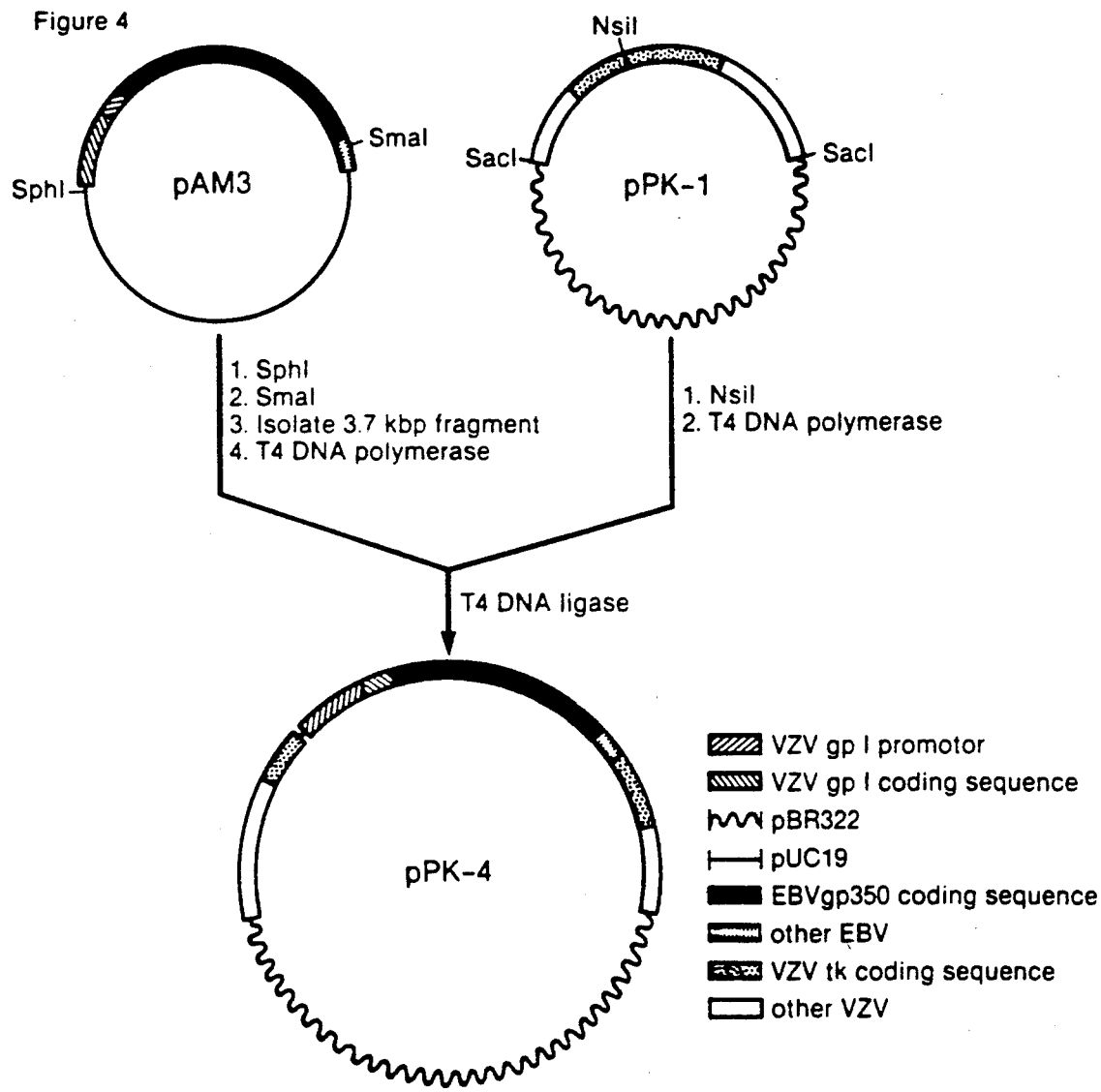

Figure 5

- VZV gp I promotor
- VZV gp I coding sequence
- pBR322
- pUC19
- EBVgp350 coding sequence
- other EBV
- VZV tk coding sequence
- other VZV
- pUC13 pPK-3

VZV Oka GENOMIC DNA

COTRANSFECTION

HUMAN CELL

HOMOLOGOUS RECOMBINATION

GENERATION OF RECOMBINANT VZV VIRAL GENOME

1. REPLICATION OF RECOMBINANT VZV VIRUS
2. EXPRESSION OF EBVgp350 ON CELL SURFACE
3. ROSETTE ASSAY
4. ISOLATE RECOMBINANT FROM ROSETTE POSITIVE pfu

VARICELLA-ZOSTER VIRUS AS A LIVE RECOMBINANT VACCINE

RELATED APPLICATIONS

This application is a continuation of U.S. Ser. No. 07/376,788, filed Jul. 7, 1989, now abandoned, which was a continuation-in-part of U.S. Ser. No. 07/276,984, filed Nov. 28, 1988, now abandoned, which was a continuation of U.S. Ser. No. 07/263,562, filed Oct. 27, 1988, now abandoned, which was a continuation of U.S. Ser. No. 07/051,444, filed May 18, 1987, now abandoned, which was a continuation-in-part of U.S. Ser. No. 07/020,617, filed Mar. 27, 1987, now abandoned, which in turn was a continuation-in-part of U.S. Ser. No. 06/876,956, filed Jun. 20, 1987, now abandoned, the priority of each being claimed herein under 35 U.S.C. §120.

BACKGROUND OF THE INVENTION

Chickenpox is caused by varicella-zoster virus (VZV), a member of the herpesvirus family. The disease occurs in people with no prior immunity to VZV. VZV-specific antibodies can be demonstrated shortly after the onset of disease, decline during convalescence, but remain detectable for many years and correlate with immunity to the disease. Chickenpox is highly contagious; over 90% of the population becomes exposed to VZV before the age of 20. In most or all cases, VZV becomes latent, possibly in dorsal root ganglion cells. From this latent state, VZV can reactivate and cause zoster even in the presence of specific antibodies, probably as a result of weakened cellular immunity. The disease is highly morbid to the immunosuppressed and to those beyond the second decade.

In 1974, Takahashi reported the isolation of the Oka strain of VZV from the vesicle of a child with chickenpox. This strain then was attenuated by passage through guinea pig embryo cells and human diploid fibroblasts. The attenuated variant of VZV/Oka has been tested clinically in thousands of youngsters. It is capable of eliciting high levels of antibodies reactive with the surface of the VZ virion. Furthermore, this strain displays protective efficacy for the prevention of chickenpox in young children and in the immune-compromised. It is noteworthy that this strain of VZV is the only available viral vaccine which can be used safely in immune-compromised patients, thus making VZV versatile for broader applications.

Epstein-Barr virus (EBV) is the etiologic agent of infectious mononucleosis. The EB virion has 3 major surface glycoproteins: gp350 (350,000 dalton glycoprotein), gp220, and gp85. The gp350 and gp220 polypeptides are the products of a single viral gene. These 2 glycoproteins are capable of eliciting the production of antibodies capable of neutralizing EBV infectivity in vitro. Therefore, the gp350 gene and its products are useful for the preparation of a vaccine to EBV-induced disease through the use of recombinant DNA techniques. Furthermore, it would be desirable to vaccinate people simultaneously against both VZV- and EBV-induced diseases, or alternatively against both VZV-induced disease and another disease.

Hepatitis B virus (HBV) is the infectious agent responsible for several varieties of human liver disease, including cirrhosis and hepatocellular carcinoma, which claims hundreds of thousands of lives per year. The HB virion is composed of two groups of structural proteins, the core proteins and the envelope or surface ("S") proteins. In addition to being the major surface proteins of the virion, i.e., Dane particle, the "S" proteins are the sole constituents of Australia antigen, or 22 nm particles. The "S" proteins are the translational products of a large open reading frame (ORF) encoding 389–400 amino acids, depending upon serotype. This ORF is demarcated into three domains, each of which begins with an ATG codon that is capable of functioning as a translational initiation site in vivo. These domains are referred to as preS-1 (108–119 amino acids), preS-2 (55 amino acids), and S (226 amino acids) in their respective 5'-3' order in the gene. The six protein products derived from this ORF have the following compositions:

1) gp42 (42,000 dalton glycoprotein)=preS-1/preS-2/S (meaning preS-1, contiguous with preS-2, contiguous with S)
2) p39 (p=protein)=preS-1/preS-2/S
3) gp36=preS-2/S (two glycosylation sites)
4) gp33=preS-2/S (one glycosylation site)
5) gp27=S (one glycosylation site)
6) p24=S (or HB surface antigen, i.e., HBsAg)

Outside of man, chimpanzees are the only species which is fully susceptible to HBV infection, as reflected in quantifiable markers such as HBs+, elevated serum levels of liver enzymes, etc. Chimpanzees have been vaccinated with three doses of purified HBsAg particles (containing p24) and then challenged with a large dose of infectious HBV. While mock-vaccinated animals have suffered the signs of acute HBV infection, the HBsAg-vaccinated animals have been protected completely from any signs of infection. Therefore, in this experimental system, HBsAg particles, composed of gp27 and p24 (S domain only), have been sufficient to induce protective immunity. Spurred by these observations, several manufacturers have produced HB vaccines composed of HBsAg particles.

Recent data have suggested that the preS-1 and preS-2 domains may play an important role in immunity to HBV infections. Both antibodies to preS-1 (elicited by immunization with a peptide consisting of amino acid residues 10–32 of preS-1) as well as antibodies to preS-2 (elicited by immunization with a peptide consisting of amino acid residues 1-26 of preS-2) are capable of blocking the binding of HBV to human hepatoma cells in vitro; anti-HBs (sera from patients vaccinated with HBsAg lacking preS-1 or preS-2) is incapable of mediating this blocking event. If this in vitro event mimics in vivo infection, then pre-S (i.e., preS-1 and preS-2 in toto linked together) domains may represent the HBV binding site to its liver cell receptor, and anti-pre-S may block HBV attachment and initiation of infection. In addition, it has been found that anti-pre-S rises in titer during the recovery phase from acute HBV infection, indicating a role for these antibodies in recovery. Finally, it has been shown that vaccination of chimpanzees with a 108 amino acid pre-S polypeptide (residues 27-119 of preS-1 contiguous with 1–16 of preS-2) was capable of mediating some measure of protection against HBV challenge. In sum, these experimental observations have suggested that the pre-S domains are a useful addition to present HB vaccines, thus highlighting the desirability of expressing the large ORF encoding preS-1/preS-2/S.

OBJECTS OF THE INVENTION

It is an object of the present invention to alter the naturally-occurring VZV genome to produce recombinant viruses carrying heterologous, i.e., non VZV-derived, viral DNA. It is a further object to utilize heterologous DNA which encodes an immunogenic polypeptide of another human viral pathogen. Yet another object is the providing of methods for expressing such heterologous viral DNA as part of the VZV genome. Still another object is the providing of a method for vaccinating humans to induce in them an immune response to heterologous polypeptides encoded by the newly introduced viral DNA. These and other objects of the present invention will be apparent from the following description.

SUMMARY OF THE INVENTION

The VZV genome has been modified by the introduction of heterologous viral DNA which encodes an immunogenic polypeptide of another human pathogen into a nonessential gene of the VZV genome or into the internal repeat sequence of the VZV genome. This heterologous polypeptide is expressed in cells infected by the recombinant virus. Since the vaccine strain of VZV, in clinical testing, is capable of preventing chickenpox in children, recombinant VZV carrying heterologous genetic material is useful as a vaccine for chickenpox as well as for heterologous pathogens.

BRIEF DESCRIPTION OF THE DRAWINGS

FIG. 4 is a schematic showing the production of pPK-4.

FIG. 5 is a schematic showing the generation of recombinant VZV.

DETAILED DESCRIPTION OF THE INVENTION

Figure 1:
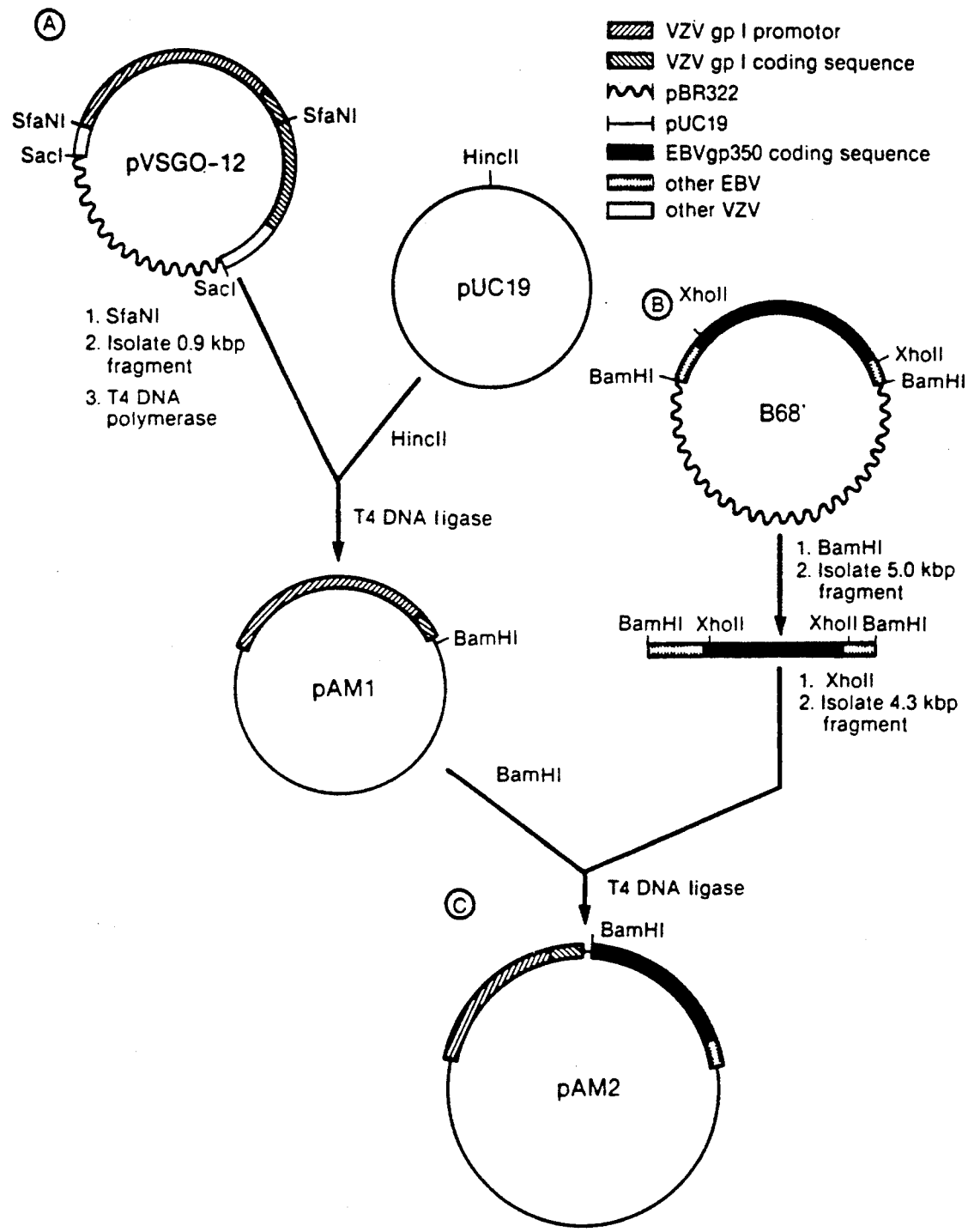
FIG. 1 is a schematic showing the production of pAM2.
Figure 2:
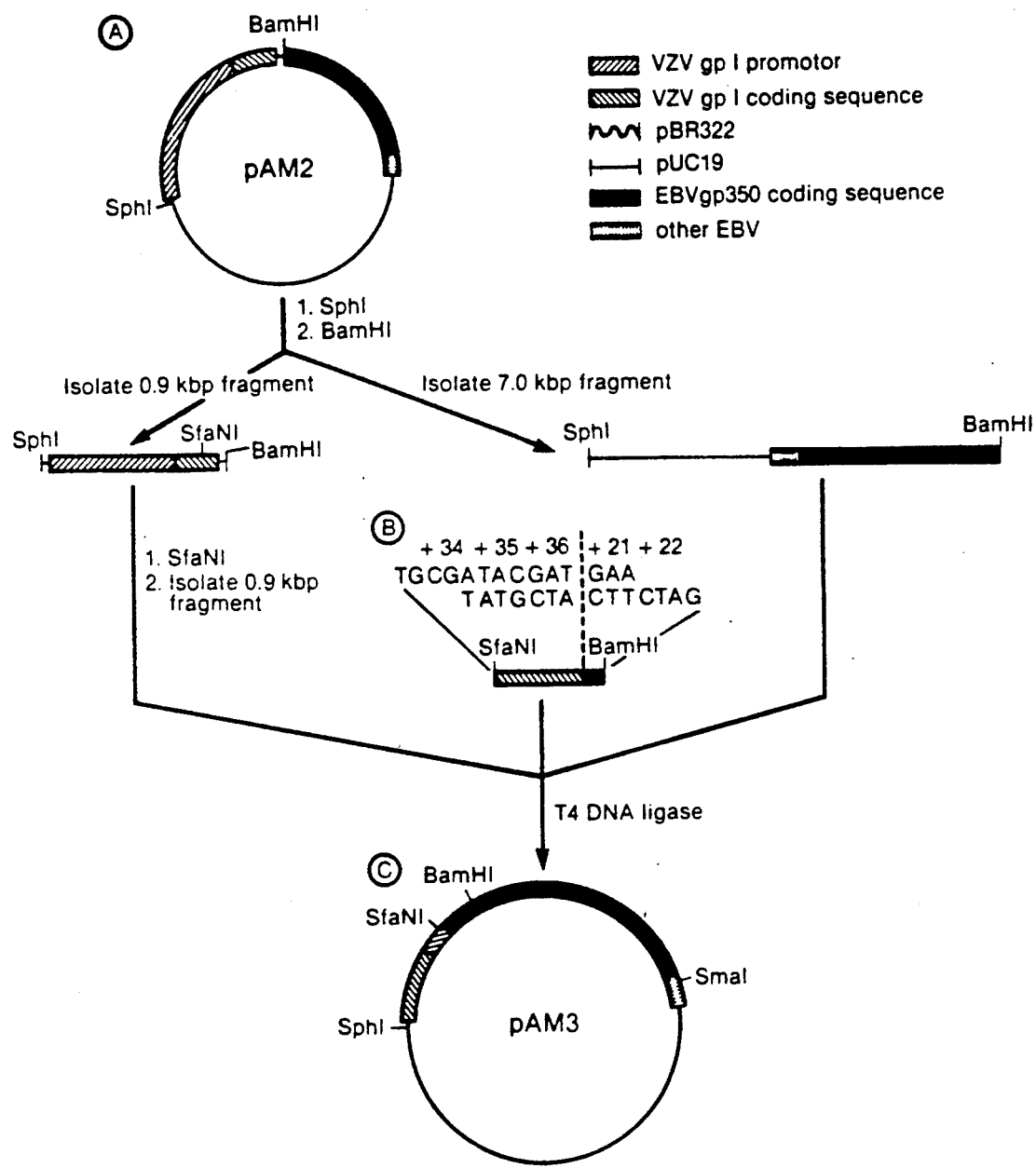
FIG. 2 is a schematic showing the production of pAM3.
Figure 3:
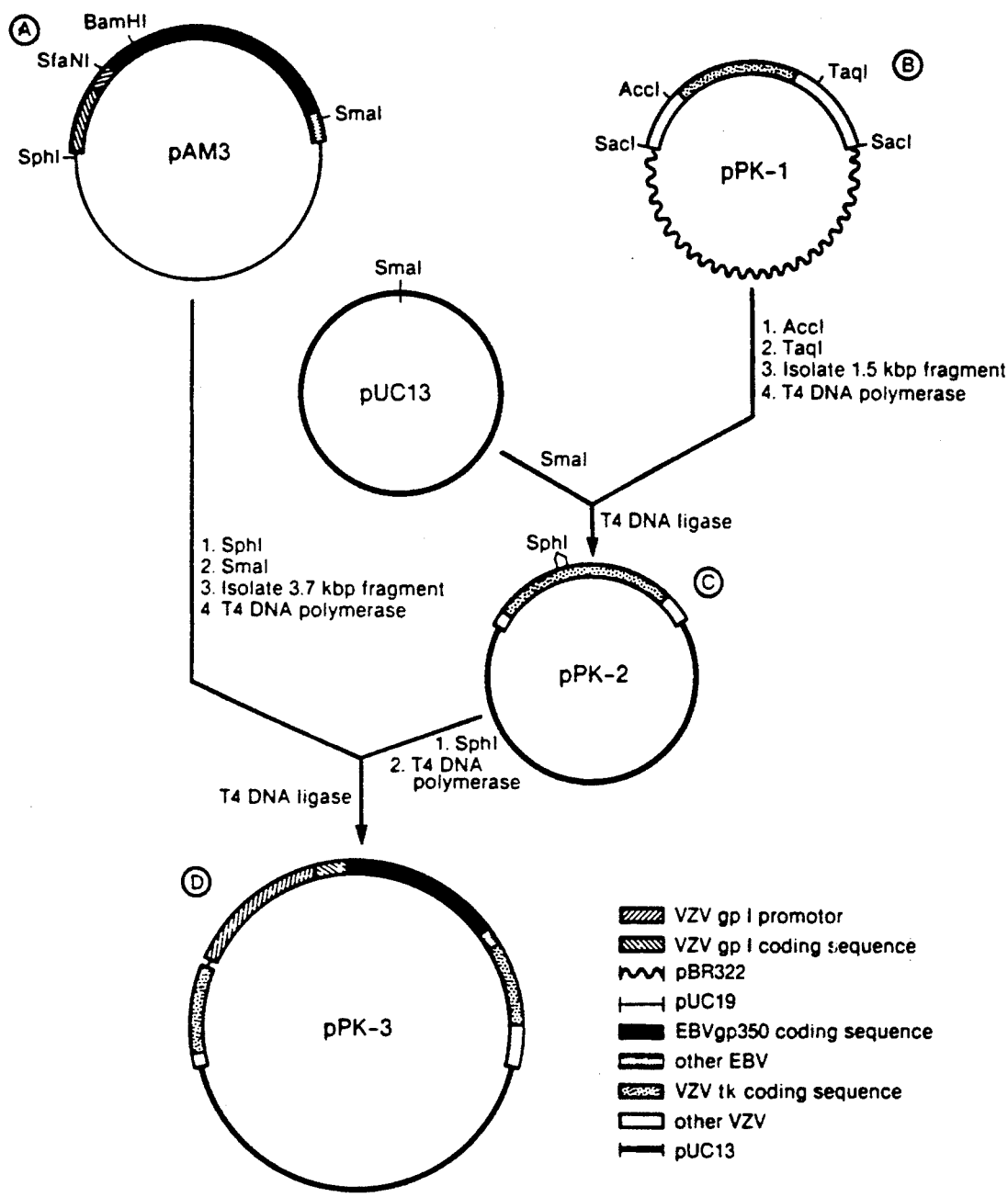
FIG. 3 is a schematic showing the production of pPK-3.

The present invention is directed to the production of recombinant VZV which can function as a vaccine both for chickenpox as well as for diseases caused by other human pathogens. In addition to its safety and efficacy profile in clinical trials of healthy children, the vaccine strain of VZV has been safe and effective in clinical trials in the immuno-compromised. It is undesirable to utilize other live attenuated viruses as vaccines in such individuals, thus affording a significant advantage to the use of VZV and its recombinant derivatives as described in the present invention.

It is advantageous to present a heterologous immunogenic polypeptide in the form of live recombinant VZV rather than as a recombinant-derived subunit vaccine for three principal reasons. Firstly, a polypeptide presented to the immune system as a replicating structure often can elicit longer-lasting immunity than when it is presented as a non-replicating, i.e., subunit structure. Secondly, a presentation on a replicating structure can elicit cell-mediated immunity more efficiently than can a presentation as a subunit structure. Finally, insofar as the heterologous polypeptide is being expressed in human cells, the polypeptide undergoes post-translational modifications most closely resembling those occurring when the polypeptide is expressed in the natural human infections by the heterologous pathogen. In contrast, the post-translational modifications upon the heterologous polypeptide expressed as a recombinant-derived product in prokaryotic or eukaryotic cells often differ from those modifications which occur when the polypeptide is expressed during the natural human infection. Furthermore, expression of the heterologous polypeptide as part of a recombinant VZV obviates any potential risks associated with the use of a live attenuated heterologous pathogen as a vaccine. This is advantageous, since such a live attenuated heterologous pathogen has the theoretical possibility of reversion to a more infectious and, therefore, pathogenic form.

The live recombinant VZV genome is derived as follows:

A DNA clone which places a naturally-occurring VZV promoter sequence immediately 5' to the non-VZV viral DNA, e.g., DNA encoding the EBV gp350 gene coding sequence is created as follows. A VZV plasmid containing the complete VZV gpI gene (including the entire 5' flanking sequences) is digested with SfaN1 and flush-ended, yielding a 0.9 kbp fragment containing the VZV gpI promoter as well as the first 34 amino acids of the gpI primary translational product. An EBV plasmid containing the gp350 gene is digested with BamHI and XhoII, yielding a 4.3 kbp fragment containing the complete gp350 coding sequence except for the first 21 amino acids. Oligonucleotides encoding amino acids 34–36 of VZV gpI as well as amino acids 21–22 of EBV gp350 are synthesized. The 0.9 kbp DNA is cloned into pUC19, digested with BamHI, and ligated with the 4.3 kbp fragment. The resulting vector (pAM2) is digested with SphI, BamHI and, SfaNI, and the resulting 0.9 and 7.0 kbp fragments are ligated with synthetic oligonucleotides, yielding pAM3. A VZV plasmid containing the thymidine kinase (tk) gene (pPK-1) is digested with AccI and TaqI, yielding a 1.5 kbp fragment containing the complete tk coding region which then is cloned into pUC13. This tk DNA clone (pPK-2) is digested with SphI and made flush-ended. Alternatively, the VZV plasmid containing the tk gene (pPK-1) is digested with NsiI and made flush-ended. pAM3 is digested with SphI and SmaI, made flush-ended, and cloned into the flush-ended SphI site of pPK-2 or the flush-ended NsiI site of pPK-1. This generates a DNA fragment containing the nonessential VZV tk gene circumscribing the VZV gpI promoter and EBV gp350 coding sequence (tk cassette).

VZV is highly cell associated and labile and produces 10,000 times less virus than Herpes Simplex Virus (HSV). Because the biology of VZV is dramatically different from HSV, techniques used with HSV to select for tk+ or tk− recombinant viruses have no utility to VZV and new methods must be invented to prepare recombinant VZV viruses. These methods include the following:

1) a method for sensitive and non-destructive identification of infected cells containing a recombinant virus 2) a method for amplification of the recombinant virus population such that upon production of cell free virus, sufficiently high titers will be achieved to allow invention of plaque pure recombinant virus 3) a method of producing cell-free virus for utility in inventing recombinant VZV.

The following describes the application of these methods to the invention of a recombinant VZV expressing EBV gp350 and are generally applicable to the isolation of any VZV expressing any heterologous antigen. Full length infections VZV genomic DNA and the tk cassette described above are cotransfected onto the MRC5 cell strain of human diploid fibroblasts. Plaques from this transfection are screened by means of specific monoclonal antibodies coupled to red blood cells which will rosette around cells infected with recombinant virus expressing EBV gp350. This method is extremely sensitive and non-destructive, features which are essential for the invention. A single plaque is identified and cylinder clones are then used to trypsinize the small numbers of cells infected with recombinant VZV and cell associated virus is passaged onto a new monolayer of MRC5 cells. Rosetting is again utilized, identifying 10–20 plaques containing mixed populations of wild type and recombinant virus. These rosette positive plaques are then cylinder cloned and passaged onto new monolayers of MRC5 cells. This method is utilized until ten 150 cm$^2$ flasks containing 80–90% rosette positive plaques are obtained. The cells are scraped from the flasks, sonicated, and filtered through a low binding 0.22 $\mu$m filter to produce cell-free virus capable of being plaque purified. Because VZV has a high affinity for cell components, failure to filter the sonicated virus results in failure to achieve plaque purification and, therefore, the application of this method is essential to the invention. Cell-free virus is used to infect monolayers of MRC5 cells and rosetting is used to detect plaque pure recombinant VZV which expresses EBV gp350; this recombinant can be passaged in the cell-free fashion and is stable upon repeated cell-associated passage. DNA hybridization analyses using EBV gp350 and VZV tk DNA probes further confirm the structure of recombinant VZV.

Dane particles are utilized as the source of HBV nucleic acid for the isolation of the preS-1/presS-2/S ORF. The endogenous polymerase reaction is employed in order to produce covalently closed circular double-stranded DNA of the HBV genome from the nicked and gapped form that resides natively in the HB virion. The repaired DNA is isolated and digested to completion with EcoRI. The *E. coli* cloning vector pBR322 also is digested with EcoRI, ligated to the HBV DNA and used to transform *E. coli*. Recombinant plasmids are selected, these containing the HBV genome in a circularly permuted form in which the EcoRI site divides the complete preS-1/preS-2/S coding region into a 5' domain of 0.4 kilobase pairs (kbp) and a 3' domain of 0.8 kbp. These two domains are subcloned for the eventual reassembly of the entire gene. For the 3' domain, pUC19 is digested with EcoRI and BamHI, then ligated to a synthetic oligonucleotide which consists of the final 5 nucleotides of the coding region, the stop codon, a HindIII site, and a BamHI end. The 3' portion of the preS-1/preS-2/S gene, consisting of a 0.8 kbp EcoRI-AccI fragment, is cloned into this vector. pUC18 is digested with HindIII and EcoRI and ligated to a 72 bp synthetic oligonucleotide which reconstitutes the complete ORF from the BamHI site upstream, through the distal ATG and a 10 bp nontranslated leader sequence, to a HindIII compatible terminus. The 0.3 kbp BamHI-EcoRI fragment of the 5' domain then is ligated into this oligonucleotide-linked cloning vector. The 5' pUC18 and 3' pUC19 clones are amplified by growth in *E. coli*, and the coding regions are digested from the isolated plasmids as HindIII-EcoRI fragments. The 5' and 3' fragments are ligated, digested with HindIII, flush-ended and the complete ORF with flush-ended termini is cloned into pUC18 which had been digested previously with BamHI and had been flush-ended.

The VZV plasmid containing the complete VZV gpI gene is digested with AvaI, and the 3.7 kbp fragment is purified by preparative agarose gel electrophoresis. Four oligonucleotides are synthesized, hybridized and ligated to form a 55 base-pair (bp) AvaI-XbaI linker. This linker is ligated to the 3.7 kbp fragment, the mixture is digested with EcoRV, and the 0.9 kbp fragment (containing the gpI promoter) is isolated by preparative agarose gel electrophoresis, flush-ended, and cloned into the SmaI site of the pUC18 vector containing preS-1/preS-2/S. This vector (containing the VZV gpI promoter and preS-1/presS-2/S coding region) is digested with SacI and PstI, flush-ended, and cloned into the flush-ended NsiI site of pPK-1. This generates a DNA fragment containing the nonessential VZV tk gene circumscribing the VZV gpI promoter and the preS-1/preS-2/S coding sequence (tk cassette).

Full-length VZV genomic DNA and the tk cassette described above are cotransfected onto MRC-5 cells. Plaques from this transfection are screened by means of monoclonal antibodies coupled to red blood cells and used to detect the presence of HBV "S" proteins. Recombinant VZV is found which expresses HBV proteins; this recombinant can be passaged in cell-free fashion and is stable upon repeated cell-associated passage. DNA hybridization analyses using appropriate DNA probes further confirm the structure of recombinant VZV.

The EBV gp350 gene is but one example of a non-VZV DNA sequence that can be inserted into the VZV genome. Often, but not always, the most useful of such sequences would be those encoding proteins on the surfaces of human pathogens, including viruses and bacteria. The EBV gp350 sequence has no intrinsic qualities which make it unique relative to other DNA sequences for recombination into the VZV genome. Thus, it is obvious to those skilled in the art that the principle of inserting the EBV gp350 gene as non-VZV DNA into the VZV genome extends to any non-VZV DNA sequence, including, but not limited to, the preS-1/preS-2/S ORF of HBV and antigenic components of HIV, e.g., gp41 and gp120. Furthermore, since the genome of VZV is very large, it is capable of accommodating a non-VZV DNA sequence of large size. Whether the non-VZV DNA has a single complete gene or more than one gene, expression of the foreign gene will occur or, if more than one gene is added, expression of several foreign genes will occur. Thus, it is obvious to those skilled in the art that the principle of inserting the EBV gp350 gene as non-VZV DNA into the VZV genome extends to more than one gene.

The VZV gpI promoter is physiologically very active during the course of a viral infection. The VZV genome contains many genes flanked by promoters which are useful for directing the synthesis of non-VZV genes, since it is well known that a coding sequence can be expressed even if flanked by a promoter from a different gene. Furthermore, numerous promoter sequences derived from mammalian cells have been described which are effective at directing foreign gene expression, such promoters including, but not limiting to, those of metallothionein, the retroviral long terminal repeat, and simian virus 40. The promoter is defined by its utility in directing gene transcription, not by its origin. Therefore, it is obvious to those skilled in the art that the choice of a promoter in the expression cassette extends to any eukaryotic, prokaryotic or viral promoter capable of directing gene transcription in cells infected by recombinant VZV.

It has been demonstrated that the tk gene is nonessential to the replication and stability of VZV. This has been demonstrated by the ability to select viable tk−VZV. Therefore, the utility of tk as an insertion point for non-VZV DNA is useful in particular with respect to its nonessential nature in VZV replication. Other regions that are nonessential to the replication and stability of VZV and, therefore, useful as insertion points for non-VZV DNA are the dUTPase gene and the internal repeat sequences (IRS). With the availability of the complete VZV genomic DNA sequence, other nonessential genes and regions can be defined and utilized, e.g., udp and irs. Therefore, it will be obvious to those skilled in the art that the choice of an insertion point for non-VZV DNA extends to any nonessential gene or region in the VZV genome that is nonessential to the replication and stability of VZV.

Vaccinia virus has been proposed for use as a vector for expressing foreign proteins, e.g., hepatitis B. It has been recognized that the use of vaccinia virus in immunocompromised individuals often leads to serious morbidity and mortality. On the other hand, the use of an attenuated strain of varicella-zoster virus as a vector for expressing foreign proteins is useful as a vaccine for immunocompromised individuals, thereby immunizing against varicella as well as a disease whose causative agent encodes the foregoing protein expressed by the vector. The vaccine may be administered by various routes including but not limited to subcutaneously and intramuscularly. Some examples of foreign proteins are those expressed by EBV, hepatitis B, human immunodeficiency virus (HIV), respiratory syncytial virus, herpes simplex virus type 1 and type 2, and cytomegalovirus. The vectors of the present invention elicit formation of protective antibodies in mammalian species, e.g. Callithrix jacchus at a dosage level of $10^2$–$10^4$ PFU per individual recipient.

The following examples illustrate the present invention without, however, limiting the same thereto. The disclosure of each reference mentioned in the following examples is hereby incorporated by reference.

EXAMPLE 1

Construction of a modified VZV tk gene containing an expression cassette encoding EBV gp350

The VZV gpI glycoprotein represents one of the major structural glycoproteins contained in the VZV virion [Ellis et al., J. Virology, 53: 81 (1985)]; the transcription rate directed by the VZV gpI promoter is relatively high. The SacI G fragment [Davison et al., J. Gen. Virol. 64: 1181 (1983)] of VZV, which circumscribes the complete gpI gene, was cloned into a modified pBR322(pRES), created by digesting pBR322 with BamHI, flush-ending with the Klenow fragment of DNA polymerase I, ligating with an octamer oligonucleotide containing the restriction site for SacI (Collaborative Research), and digesting with SacI. The resulting plasmid (pVSGO-12) was digested with SfaN1, and the 0.9 kbp fragment containing the upstream promoter sequences and coding region for the first 34 amino acids of VZV gpI was purified by preparative agarose gel electrophoresis (FIG. 1A). The 0.9 kbp fragment was flush-ended with T4 DNA polymerase and cloned into the HincII site of pUC19 [Yanisch-Perran et al., Gene 33: 103 (1985)], thus forming pAM1. The structural gene for EBV gp350 and gp220 is identical and is wholly contained within the BamHI-L genomic DNA fragment of plasmid B68' [Hummel et al., J. Virology 49: 413 (1984)]. The B68' plasmid containing BamHI-L was digested with BamHI, and the 5.0 kbp BamHI-L fragment was purified by preparative agarose gel electrophoresis. This fragment then was digested with XhoII and the 4.3 kbp fragment containing the entire structural gene except for the first 63 bp of the gp350 coding region, but including the transcriptional termination sequence, was purified by preparative agarose gel electrophoresis (FIG. 1B). pAM1 was digested with BamHI and ligated with the 4.3 kbp fragment. The resulting plasmid (pAM2, FIG. 1C) was digested with SphI and BamHI and the 0.9 kbp and the 7.0 kbp fragments were purified by preparative agarose gel electrophoresis (FIG. 2A). The 0.9 kbp fragment was digested with SfaN1, which generated another 0.9 kbp fragment that was isolated by preparative agarose gel electrophoresis.

An oligonucleotide linker containing the following sequence was synthesized (FIG. 2B):

```
5'-TGCGATACGATGAA
        TATGCTACTTCTAG-5'
```

This linker contains SfaN1 and BamHI 5' overhangs and represents the coding sequence for amino acids 34–36 of the VZV gpI gene followed by amino acids 21–22 of EBV gp350. The linker, the 0.9 kbp fragment, and the 7.0 kbp fragment were ligated together. The resulting plasmid (pAM3, FIG. 2C) was digested with SphI and SmaI, and the 3.7 kbp fragment was purified by preparative agarose gel electrophoresis and subsequently flush-ended with T4 DNA polymerase (FIG. 3A). The SacI H fragment [Davison et al., J. Gen. Virol. 64:1181 (1983)] of VZV, which circumscribes the complete tk gene, was cloned into pRES. The resulting plasmid (pPK-1) was digested with AccI and TaqI, generating a 1.5 kbp fragment containing the entire coding region for tk (FIG. 3B). This fragment was purified by preparative agarose gel electrophoresis, flush-ended with T4 DNA polymerase, and cloned into the SmaI site of pUC13 [Pharmacia Inc., 1984 Catalog #27-4954-01]. The resulting plasmid (pPK-2, FIG. 3C) was digested with SphI, which digests twice within the tk coding sequence, flush-ended with T4 DNA polymerase, and ligated with the 3.7 kbp fragment. The resulting plasmid (pPK-3, FIG. 3D) contains the VZV gpI/EBV gp350 expression cassette within the VZV tk gene. pPK-3 was used to generate a recombinant VZV expressing EBV gp350, as described in Example 3, and contains the following salient features: 1) VZV tk flanking sequences for the generation of homologous recombination between VZV DNA and the recombinant plasmid. 2) the VZV gpI promoter for directing high levels of expression of EBV gp350 during viral replication. 3) the VZV gpI leader sequence for insertion of gp350 into the rough endoplasmic reticulum and expression on the plasma membrane of infected cells. 4) gp350 coding region for the expression of EBV gp350 proteins. 5) gp350 membrane anchor, translational termination and polyA-addition sequences.

EXAMPLE 2

Construction of another modified VZV tk Gene containing an expression cassette encoding EBV gp350 pAM3 (Example 1) was digested with SphI and SmaI, and the 3.7 kbp fragment was purified by preparative agarose gel electrophoresis and subsequently flush-ended with T4 DNA polymerase (FIG. 4). pPK-1 (Example 1) was digested with NsiI, flush-ended with T4 DNA polymerase, and ligated to the 3.7 kbp fragment of pAM3. The resulting plasmid (pPK-4) contains the VZV gp1/EBV gp350 expression cassette within the VZV tk gene. pPK-4 was used to generate a recombinant VZV expressing EBV gp350 as described in Example 3 and contains the same salient features as pPK-3 (Example 1) with the following exception: The tk flanking sequences were extended to include the entire VZV SacI H fragment, increasing the 5' flanking sequence by 3.7 kbp and the 3' flanking sequence by 0.6 kbp, relative to pPK-3.

EXAMPLE 3

Generation of VZV recombinant virus expressing EBMA

One µg each of VZV/Oka genomic DNA and pPK-3 or pPK-4 in 200 µl of 2 X HBS (274 mM NaCl, 10 mM KCl, 1.4 mM $Na_2HPO_4$, 12 mM dextrose, 42 mM Hepes, pH 6.9) plus sterile distilled water (to a final volume of 380 µl) was added to a 12×75 mm tube. Twenty µl of 2M calcium phosphate, 10 mM Hepes, pH 5.5, then was added and a DNA coprecipitate was allowed to form for 30 minutes at 23° C. The precipitate was added to 1.5 ml growth media [Dulbecco's Modified Eagle's Medium (DMEM) plus 10% fetal calf serum] covering MRC-5 cells, set up the previous day at $3\times10^5$ cells/35 mm tissue culture plate, and incubated for 4 hours in a 37° C. $CO_2$ incubator (FIG. 5). The media were removed, the cells were washed with 1 ml growth media, and 15% glycerol in 1 X HBS was applied to the cells for 3 minutes. The cells were washed once more with growth media and incubated in 1.5 ml growth media for 24 hours in a 37° C. $CO_2$ incubator. The cells then were trypsinized and passaged into 2 60 mm plates containing 4 ml growth media per plate and incubated in a 37° C. $CO_2$ incubator until viral plaques were observed. Five to 10 days later, cells containing replicating virus, as indicated by the presence of cytopathicity, were trypsinized and passaged cell-associated onto a 80-90% confluent monolayer of MRC-5 cells. Two days later, when viral plaques were evident, the growth media were replaced by fresh growth media containing 10 µg/ml of a monoclonal antibody (McAb) specific for EBV gp350 [Cl.4, Thorley-Lawson et al., Proc. Nat. Acad. Sci. USA, 77:5307 (1980)] and incubated for 1 hour at 37° C. The cells then were washed 3 times with DMEM and incubated for 1 hour at 37° C. in the presence of growth media containing human red blood cells to which rabbit anti-mouse immunoglobulin had been coupled according to the following procedure: Human red blood cells (type AB positive) were washed 5 times at 23° C. in 150 mM NaCl. Two ml of rabbit anti-mouse IgG (1 mg/ml) were added with gentle vortexing to 1 ml of washed and packed red blood cells. Two ml of 0.033% (w/v) chromic chloride, pH 5.0, were added dropwise to the red blood cells with constant mixing. The cells then were rocked for 7 minutes at 23° C., washed 5 times at 4° C. in saline solution, washed 1 time at 4° C. in Hank's Balanced Salt Solution (HBSS), and resuspended in 50 ml HBSS for use at a 1:10 dilution. After 1 hour of incubation, the virally-infected cells were washed 3 more times with DMEM and screened visually for the formation on the VZV plaques of rosettes of red blood cells; such rosettes are indicative of cells expressing gp350. Approximately 10% of the plaques were rosette-positive using the Cl.4 McAb. Two other gp350-specific McAb designated 2L10 and BMA-17 and one anti-EBV+ polyclonal human serum also elicited rosette formation, while normal human serum did not. Antibodies to gp350 were not able to elicit rosette formation on plaques generated by transfection of VZV/Oka alone. A McAb directed against hepatitis A virus VPI was unable to elicit rosette formation on recombinant VZV plaques, thus indicating the specificity of this assay for the detection of gp350 expression. Cylinder clones were used to trypsinize cells infected with recombinant VZV and cell-associated virus was passaged onto a new monolayer of MRC5 cells. Rosetting was used to identify the increased numbers of rosette positive plaques containing recombinant VZV. These plaques were again passaged onto new monolayers of MRC5 cells and amplification of the plaques containing recombinant VZV was continued until ten 150 $cm^2$ flasks containing 80-90% rosette positive plaques were obtained. The cells were scraped from the flasks. Cell-free virus was generated by sonicating infected cells for 2 minutes at 4° C. in DMEM and passing the sonicated supernatant through a low-binding 0.22 µm filter. The recombinant VZV expressing EBV gp350 can be passaged as cell-free infectious virus. Once the recombinant VZV has been plaque purified, 0.01% of 5-bromo-2'-deoxyuridine is used to confirm that recombination has occurred within the tk gene and support the data obtained by Southern blot hybridization. In addition, the recombinant VZV has been passaged in cell-associated form for more than 30 passages without abrogation of its ability to express EBV gp350, as judged by binding to the 3 anti-gp350 McAb mentioned above.

Lysates were prepared from MRC-5 cells infected with either recombinant VZV or parental VZV/Oka, electrophoresed in 6% polyacrylamide gels, and Western blotted to nitrocellulose. With the use of an anti-EBV+ polyclonal human serum, gp350 and gp220 were found to be present in the recombinant VZV-infected cell extract but not in the parental VZV-infected cell extract. These glycoproteins comigrated with gp350 and gp220 produced in mouse L cells stably transfected with a eukaryotic expression plasmid for gp350. VZV genomic DNA from recombinant and parental viruses then was characterized by Southern blot analysis. Purified viral DNA, 20 µg, was digested with BglII, HpaI, KpnI, or SalI, electrophoresed on a 0.8% agarose gel, transferred to nitrocellulose and probed with DNA from the gp350 gene which had been labelled with $\alpha[^{32}P]dCTP$ by nick-translation. Only DNA fragments present in the lanes containing the recombinant VZV hybridized to the gp350 probe, demonstrating the linkage of the gp350 gene within the VZV genome.

EXAMPLE 4

Construction of a modified VZV tk gene containing an expression cassette encoding HBV preS-1/preS-2/S Dane particles (subtype ayw) are purified from the plasma of infected individuals by established techniques [Landers et al., J. Virology 23: 368 (1977)]. The HBV genomic DNA resides in a nicked, gapped form in the virion [Hruska et al., J. Virology 21: 666 (1977)]. In order to prepare this DNA for molecular cloning, the endogenous polymerase reaction is employed to produce covalent closed circular double-stranded DNA [Landers et al., J. Virology 23: 368 (1977)]. The DNA is deproteinized by incubation in buffer containing sodium dodecyl sulfate and, Proteinase K followed by extraction with phenol: chloroform:isoamyl alcohol (25:24:1) and concentration by ethanol precipitation. This purified DNA is digested to completion with EcoRI. The *E. coli* cloning vector pBR322 also is digested with EcoRI, ligated to the digested HBV DNA and used to transform *E. coli*. Recombinant plasmids are isolated which contain the HBV genome in a circularly permuted orientation about the unique EcoRI site, which divides the complete preS-1/preS-2/S coding region into a 5' domain of 0.4 kbp and a 3' domain of 0.8 kbp [Galibert et al., Nature 281: 646 (1979)]. These two domains are subcloned for the eventual reassembly of the entire gene. pUC19 is digested with EcoRI and BamHI, then ligated to a synthetic oligonucleotide which consists of the final 5 nucleotides of the coding region, the stop codon, a HindIII site, and a BamHI end. The structure of this oligonucleotide is:

```
    ATACATTTAAAGCTTG
    TGTAAATTTCGAACCTAG
```

The 3' portion of the preS-1/preS-2/S gene, consisting of a 0.8 kbp EcoRI-AccI fragment is cloned into this vector (pUC19/DSD). pUC18 [Yanisch-Perran et al., Gene 33:103 (1985)] is digested with HindIII and EcoRI and ligated to 72 bp synthetic oligonucleotide which reconstitutes the complete ORF from the BamHI site upstream to the distal ATG through a 10 bp nontranslated leader sequence to a HindIII compatible terminus. The structure of this oligonucleotide is:

```
*
AGCTTACAAAACAAAATGGGGCAGAATCTTTCCACCAG-
CAATCCTCTGGGATTTT
T
    ATGTTTTGTTTTACCCCGTCT-
TAGAAAGGTGGTCGTTAGGAGACCCTAAAA
A

TCCCGACCACCAGTTG
AGGGCTGGTGGTCAACCTAG
```
(*the natural sequence contains C rather than T; The above change destroys the HinfI site without changing the encoded amino acid.)

The 0.4 kbp BamHI-EcoRI fragment of the 5' domain then is ligated into this oligonucleotide-linked cloning vector (pUC19/DSD). The 5' pUC18 and 3' pUC19 clones are amplified by growth in *E. coli*, and the coding regions are digested from the isolated plasmids as HindIII-EcoRI fragments. These fragments are ligated, digested with HindIII, flush-ended with the PolI fragment of DNA polymerase I, and the complete ORF with flush-ended termini is cloned into pUC18 which has been digested with BamHI and flush-ended with the PolI fragment of DNA polymerase I (pUC18/PSSC).

For deriving a fragment containing the VZV gpI promoter, pVSGO-12 is digested with AvaI, and the 3.7 kbp fragment is purified by preparative agarose gel electrophoresis. This fragment contains the VZV gpI promoter sequences excluding 0.05 kbp immediately 5' to the ATG translational initiation codon of VZV gpI. Four oligonucleotides with the following sequences are synthesized:

```
1# 5'-TCGGGCGAATTGCGTGGTTTTAAG
#2       CGCTTAACGCACCAAAATTCACTGAT-5'
#3 5'-TGACTATATTCCGAGGGTCGCCTGTAT
#4             ATAAGGCTCCCAGCGGACATAGATC-5'
```

Oligonucleotides #1 and #2 are hybridized as are oligonucleotides #3 and #4. The two pairs then are ligated to each other, generating a 55 bp linker containing AvaI and XbaI 5' overhangs, which represents the VZV gpI promoter sequence immediately 5' to the coding sequence of VZV gpI. This 55 bp linker is ligated to the 3.7 kbp fragment of pVSGO-12, the mixture is digested with EcoRV, and the 0.9 kbp fragment is purified by preparative agarose gel electrophoresis and subsequently flush-ended with T4 DNA polymerase. The purified 0.9 kbp fragment then is cloned into the SmaI site of pUC18/PSSC. This vector (containing the VZV gpI promoter and preS-1/preS-2/S coding region) is digested with SacI and PstI, flush-ended with T4 DNA polymerase, and cloned into the flush-ended (by T4 DNA polymerase) NsiI site of pPK-1, thus generating pPK-5. This plasmid (pPK-5) is used to generate a vero cell line expressing HBV preS1/ preS2/S which contains the following salient features: 1) the VZV gpI promoter and RNA cap site; 2) the complete protein coding sequence for HBV preS1/preS2/S; and 3) sequence for transcriptional termination and PolyA addition.

EXAMPLE 5

Generation of recombinant VZV expressing HBV preS-1/preS-2/S

One μg each of pPK-5 and VZV/Oka genomic DNA are coprecipitated and added to MRC-5 cells exactly as described in Example 3. Cells infected with recombinant VZV are screened for the production of HBV preS-1/preS-2/S by means of a specific antibody and indicator human red blood cells exactly as described in Example 3, resulting in the identification of approximately 10% of the plaques as positive for HBV preS-1/preS-2/S. Antibodies to HBV "S" proteins are not able to elicit rosette formation on plaques generated by transfection of VZV/Oka alone. A McAb directed against hepatitis A virus VPI is unable to elicit rosette formation on recombinant VZV plaques, thus indicating the specificity of this assay for the detection of preS-1/preS-2/S expression. Cell-free virus is generated by sonicating infected cells for 2 minutes at 4° C. in DMEM and passing the sonicated supernatant through a 0.22 μm filter. The recombinant VZV expressing HBV preS-1/preS-2/S can be passaged as cell-free infectious virus, and such clones can be passaged in the presence of 0.01% (w/v) 5-bromo-2-deoxyuridine, thus demonstrating recombination within the tk gene. Expression is verified further by the detection of HbsAg by AUSRIA ® (Abbott) reactivity in culture lysates.

Lysates are prepared from MRC-5 cells infected with either recombinant VZV or parental VZV/Oka, electrophoresed in 6% polyacrylamide gels, and Western blotted to nitrocellulose. With the use of an anti-HBV "S" protein serum as well as an anti-preS serum, preS-1/preS-2/S proteins are found to be present in the recombinant VZV-infected cell extract but not in the parental VZV-infected cell extract. These proteins comigrate with "S" proteins derived from HBV Dane particles. VZV genomic DNA from recombinant and parental viruses then is characterized by Southern blot analysis. Purified viral DNA, 20 μg, is digested with BglII, HpaI, KpnI, or SalI, electrophoresed on a 0.8% agarose gel, transferred to nitrocellulose and probed with DNA from the HBV preS1/preS2/S gene which has been labelled with α[$^{32}$P]dCTP by nick-translation. Only DNA fragments present in the lanes containing the recombinant VZV hybridize to the pg350 probe, demonstrating the linkage of the HBV preS1/preS2/S gene within the VZV genome.

EXAMPLE 6

The cell-free virus generated according to example 3 by sonicating infected cells is administered subcutaneously to a group of 4 *Callithrix jacchus* monkeys at a dosage level of 10 PFU/animal. A saline placebo is administered subcutaneously to a control group of 4 more *Callithrix jacchus* monkeys. After 30 days both groups are challenged with $10^8$ PFU of EBV. During an observation period of 6 months following challenge, none of the first group of monkeys shows any sign of replication of EBV while all animals in the control exhibit signs of EBV replication. This result demonstrates development of an immune response in the first group prior to challenge.

EXAMPLE 7

The cell-free virus generated according to Example 3 by sonicating infected cells is administered intranasally to a group of 3 *Saguinus oedipus* marmosets at a cloning level of $5 \times 10^6$ PFU/animal. A standard VZV is administered intranasally to a group of 3 more *Saguinus oedipus* marmosets. After 42 days all animals demonstrated antibody against VZV antigen. Further, animals which received the virus generated according to Example 3 demonstrated antibodies against the EBV component. This result demonstrates the ability of the virus generated according to Example 3 to induce an immune response which is necessary for its utility as a recombinant vaccine.

What is claimed is:

1. VZV modified by the presence in a nonessential gene or region of its genome of non-VZV viral DNA whose coding sequence specifies an immunogenic protein of a human pathogen.

2. VZV as in claim 1 wherein the non-VZV viral DNA contains the coding sequence for a polypeptide adjacent to a VZV promoter sequence adapted to direct transcription of the non-VZV DNA.

3. VZV as in claim 2 wherein the coding sequence specifies a polypeptide of Epstein Barr virus gp350 or hepatitis B virus.

4. VZV as in claim 3 wherein the coding sequence specifies a HBV preS1/preS2/S polypeptide.

5. VZV as in claim 2 wherein the promoter is the promoter which regulates transcription of the VZV gpI gene.

6. VZV as in claim 1 wherein the non-VZV viral DNA contains more than one coding sequence, each sequence encoding a different polypeptide and each sequence being adjacent to a promoter sequence adapted to direct transcription of the adjacent non-VZV viral DNA.

7. A method for producing VZV modified by the presence in a nonessential gene or region of its genome of non-VZV viral DNA whose coding sequence specifies an immunogenic protein of a human pathogen, which comprises applying to a cell monolayer a medium containing VZV and non-VZV DNA, wherein the non-VZV DNA is linked to sequences colinear with DNA present in a nonessential gene or region of the VZV genome, detecting cells infected with recombinant VZV, amplifying the cells infected with recombinant VZV, and sonicating and filtering the resultant cell monolayer, whereby plaque pure recombinant VZV is isolated.

8. A method according to claim 7 wherein the nonessential gene is the thymidine kinase gene or the dUT-Pase gene.

9. A method according to claim 7 wherein the nonessential region is the internal repeat sequence IRS.

10. A vaccine containing VZV as in claim 3.

11. A vaccine containing VZV as in claim 4.

12. A method of immunizing against chicken-pox and at least one other pathogen comprising administering to a member of a susceptible species the product of claim 1 in an amount effective to induce an immune response.

13. A method according to claim 12 wherein the member of a susceptible species is immunocompromised.

* * * * *